United States Patent
Weihrauch

(12) 
(10) Patent No.: US 6,672,316 B1
(45) Date of Patent: Jan. 6, 2004

(54) CLEANING ELEMENT, ESPECIALLY FOR CLEANING TEETH AND A METHOD FOR PRODUCING THE SAME

(75) Inventor: Georg Weihrauch, Wald-Michelbach (DE)

(73) Assignee: Coronet-Werke GmbH, Wald-Michelbach (DE)

( * ) Notice: Subject to any disclaimer, the term of this patent is extended or adjusted under 35 U.S.C. 154(b) by 0 days.

(21) Appl. No.: 09/913,534

(22) PCT Filed: Feb. 17, 2000

(86) PCT No.: PCT/EP00/01295

§ 371 (c)(1),
(2), (4) Date: Aug. 15, 2001

(87) PCT Pub. No.: WO00/49965

PCT Pub. Date: Aug. 31, 2000

(30) Foreign Application Priority Data

Feb. 25, 1999 (DE) ............................................ 199 08 238

(51) Int. Cl.⁷ ................................................ A61C 15/00
(52) U.S. Cl. ....................................................... 132/321
(58) Field of Search ............................... 132/321, 329, 132/323, 324, 325, 326, 327; 264/2.5

(56) References Cited

U.S. PATENT DOCUMENTS

| | | | |
|---|---|---|---|
| 1,637,153 A | | 7/1927 | Lawton |
| 1,989,895 A | * | 2/1935 | Van Gilder ................. 132/321 |
| 3,744,499 A | | 7/1973 | Wells |
| 3,942,539 A | | 3/1976 | Corliss |
| 4,006,750 A | * | 2/1977 | Chodorow .................. 132/323 |
| 4,142,538 A | * | 3/1979 | Thornton .................... 132/321 |
| 4,550,741 A | | 11/1985 | Krag |
| 4,836,226 A | | 6/1989 | Wolak |
| 4,922,936 A | | 5/1990 | Buzzi |
| 4,974,615 A | * | 12/1990 | Doundoulakis ............. 132/321 |
| 5,044,041 A | * | 9/1991 | Ljungberg ................... 15/210 |
| 5,086,792 A | | 2/1992 | Chodorow |
| 5,159,943 A | | 11/1992 | Richards |
| 5,289,836 A | | 3/1994 | Peng |
| 5,316,028 A | | 5/1994 | Flemming |
| 5,433,226 A | | 7/1995 | Burch |
| 5,682,911 A | | 11/1997 | Harada |
| 5,775,346 A | | 7/1998 | Szyszkowski |

FOREIGN PATENT DOCUMENTS

| | | |
|---|---|---|
| CH | 5 31 881 | 2/1973 |
| DE | 29 22 824 | 12/1979 |
| DE | 31 28 749 | 5/1982 |
| DE | 31 16 189 | 12/1982 |
| DE | 90 13 834 | 12/1990 |
| DE | 92 02 508 | 4/1992 |
| DE | 93 03 673 | 5/1993 |
| DE | 295 09 846 | 9/1995 |
| DE | 196 43 931 | 4/1998 |
| EP | 06 80 707 | 11/1995 |
| FR | 26 77 537 | 12/1992 |
| WO | WO 98 06 350 | 2/1998 |

* cited by examiner

Primary Examiner—Cary E. O'Connor
(74) Attorney, Agent, or Firm—Paul Vincent

(57) ABSTRACT

A cleaning element, in particular for cleaning teeth, comprises a flexible thread-like endless carrier, wherein at least sections thereof comprise radially protruding structured elements. To ensure reliable but gentle cleaning of the tooth surfaces, the structured elements are made from an elastomeric plastic which is preferably injection molded onto the endless carrier. A plurality of support bodies made from this elastomeric plastic can be provided on the endless carrier, spaced apart from one another, the outer surfaces of which bear the structured elements in the form of radially projecting nubs, bristles or ribs.

22 Claims, 2 Drawing Sheets

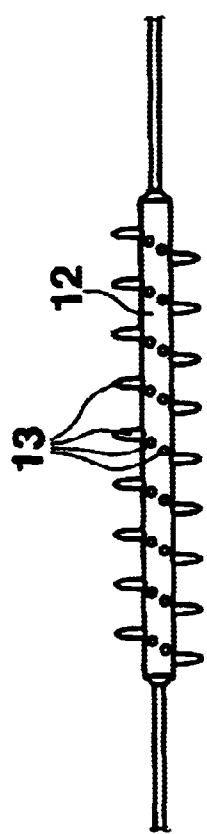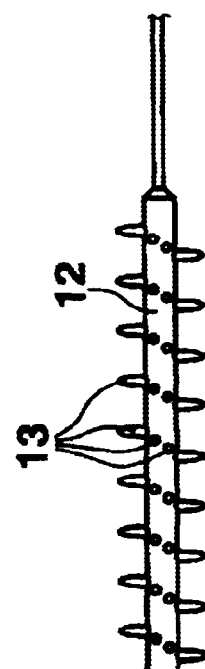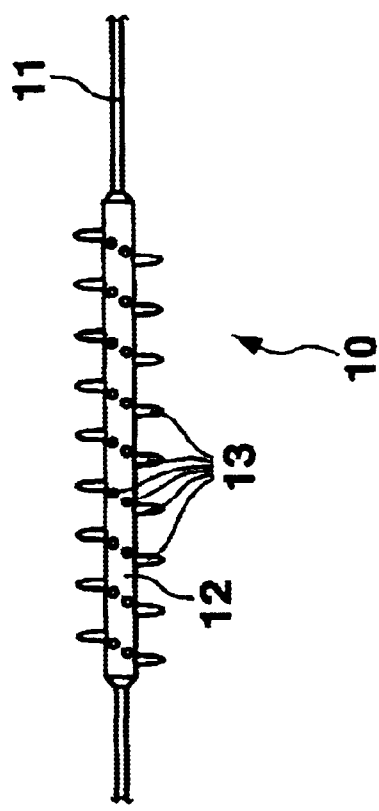

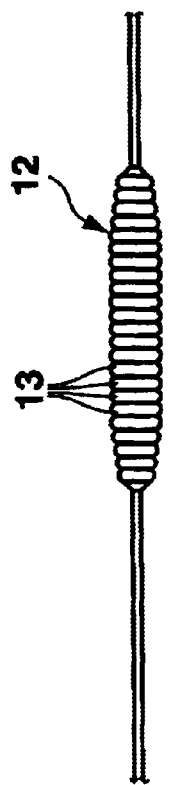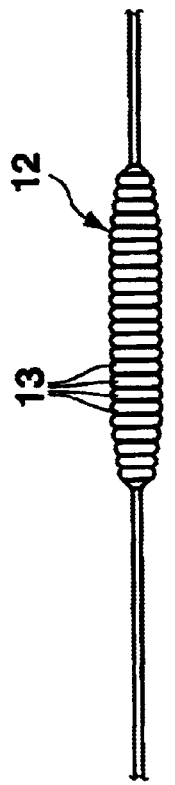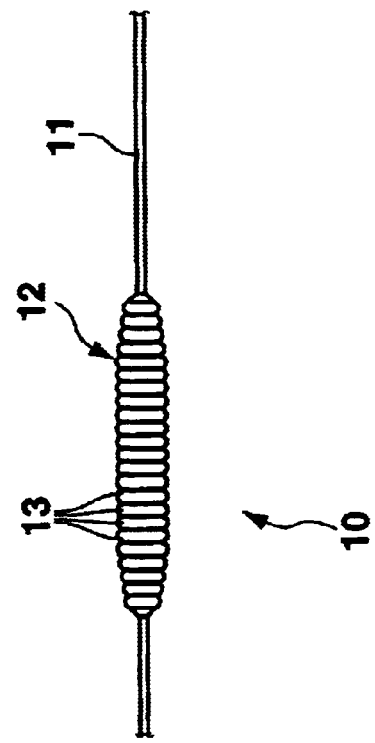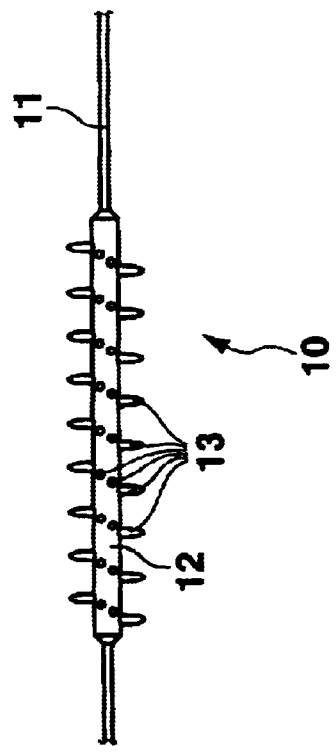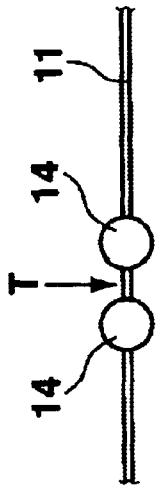

CLEANING ELEMENT, ESPECIALLY FOR CLEANING TEETH AND A METHOD FOR PRODUCING THE SAME

Translation of PCT/EP00/01295 as filed on Feb. 17, 2000

BACKGROUND OF THE INVENTION

The invention concerns a cleaning element, in particular for cleaning teeth, and a method of producing this cleaning element.

Science has proved that cleaning of the interdental spaces is particularly important for keeping teeth, and especially the tooth supporting tissue, healthy, since gum diseases and diseases of tooth supporting tissue, so-called paradontitis, usually originate in the interdental spaces. A major cause of such diseases is insufficient cleaning of the interdental spaces which may even result in bone degeneration. Satisfactory cleaning of the interdental spaces using manual or electric tooth brushes is not possible, since only approximately ⅗ of all tooth surfaces can be reached for cleaning with a toothbrush. Special cleaning devices must therefore be used.

Interdental cleaning means in the form of interdental brushes or toothpicks are often used for cleaning the interdental spaces, wherein the latter are used in particular for cleaning the easily accessible interdental space between bridge ends and in the sulcus region. Various embodiments of conventional toothpicks are made from differing materials and have differing surface configurations. The main disadvantage of a toothpick is that it contacts and treats the surfaces of the teeth in the interdental area in a merely tangential or point-like manner and cleaning of the entire surface of the tooth is not possible.

In addition to the toothpicks mentioned, cleaning threads, i.e. dental floss, have also been used for some time which are introduced into the interdental spaces and pulled over the surface of the teeth. Although dental floss can be used to clean plaque from locations which are inaccessible with brushes, and although dental floss is acknowledged by dentists to be the best cleaning method, it has not gained a sufficient degree of acceptance with the general public. One reason therefor is that handling of the dental floss is considered to be complicated by the untrained user and initial improper use often leads to painful injuries, e.g. with the dental floss cutting into the gums.

Dental floss usually consists of a thread-like endless carrier which may be a monofile, a multifile, a thread or a tape, etc. The endless carrier may be waxed and, optionally, fluoridated. Most of the dental floss available on the market is completely or at least partially enclosed along its length with a flock by applying a glue layer onto the endless carrier into which microfibers or microbristles are embedded. However, it has turned out that the polymer fibers forming the flock are not fixed on the endless carrier in an abrasion-proof manner and may become detached during use causing discomfort to the users. Moreover, scientific studies prove that the detached fibers are damaging to the health should they enter into the body. In order to avoid these disadvantages, one has attempted to develop sliding, non-fraying dental floss. However, when the dental floss slides across the tooth surfaces, it does not effect a brushing action and only a limited amount of cleaning can be achieved. To prevent the dental floss from cutting into the gums (or to at least reduce this danger), the dental floss would have to have a larger diameter. This would, however, make the dental floss excessively thick and it could no longer be introduced into all interdental spaces.

It is the underlying purpose of the invention to create a cleaning element, in particular for cleaning teeth, of the mentioned kind which ensures reliable and gentle cleaning of the tooth surfaces. Moreover, a method should be created for manufacturing the cleaning element quickly and inexpensively.

SUMMARY OF THE INVENTION

With regard to the cleaning element, the above-mentioned objective is achieved with structured elements made from an elastomeric plastic. A cleaning element is thereby produced which generates a brushing effect and associated high cleaning action on the tooth surface. The yielding, flexible material guarantees gentle treatment. Moreover, the flexibility of the plastic ensures that the cleaning element can penetrate into narrow spaces without cutting into the gum. The thread-like endless carrier may be made from conventional thread, twisted thread, wire, a multifile, a monofile, a tape, a wick or the like.

Appropriate selection of the material for the endless carrier and the structured elements permits the structured elements to be applied directly onto the endless carrier and be fixed thereto. In a preferred embodiment of the invention, the endless carrier is provided with a plurality of support bodies made from the elastomeric plastic which are spaced apart from one another, and which support the structured elements, preferably as a single piece, on their outer surfaces. The support body encloses sections of the endless carrier and simultaneously serves as the base and mounting for the above-mentioned structured elements, which extend radially outwardly in differing directions. The support body and the structured elements can thereby be produced in a simple manner by injection molding onto the endless carrier using a one or multiple component injection molding procedure.

Should the endless carrier have a certain transverse elasticity, as is particularly the case with a multifile or a thread, the endless carrier is compressed in the transverse direction by the high pressure with which the elastomeric plastic is injection molded. This leads to an advantageous reduction in the diameter of the endless carrier in the region of the injection molded plastic which is thereby additionally secured with respect to axial displacement in the longitudinal direction of the endless carrier. An adhesion promoter can optionally be applied to the surface of the endless carrier before the plastic is injection molded thereon.

The portions of the endless carrier located between the support bodies, spaced apart in the longitudinal direction of the endless carrier, may remain untreated. However, it is also possible to enclose these sections disposed between neighboring support bodies with the elastomeric plastic, wherein, in this event, these areas do not have structured elements.

The structured elements are preferably formed by radially projecting nubs and/or bristles and/or ribs. In addition thereto or as an alternative, the outer surface of the support body may be corrugated and/or fluted. In addition, a circumferential helical rib can be disposed on the support body.

In a further development of the invention, the support body has a round, oval or polygonal-shaped cross-section to increase the cleaning effect. Alternatively, it may also be configured as a flat tape.

An essential feature of the cleaning element according to the invention, is that the structured elements and, optionally, also the support body can be elastically deformed in the transverse direction of the endless carrier. This elastic shaping capability can be achieved through the intrinsic elasticity of the elastomeric plastic. In a further development of the invention, cavities may be formed in the plastic of the support body and/or the structured elements to improve the radial shaping capability. The cavities may be open or closed to facilitate compression of the structured elements when the cleaning device is inserted into narrow dental spaces. Moreover, the cavities may also comprise a cell structure by e.g. foaming the elastomeric plastic. The foaming may create a closed or also a permeable surface structure.

The cavities may also be used to accommodate medical care products and/or a lubricating agent and/or an abrasive agent. The care products may e.g. be tooth paste. Should the cavities be closed, they can be filled with fine hollow needles, wherein the injection holes close after filling due to the intrinsic elasticity of the material, while permitting release of the injected medium upon exertion of pressure.

In addition thereto or as an alternative, a medical care product and/or a lubricating agent and/or an abrasive agent may be applied to the outer side of the support body and/or the structured elements. Corresponding means may also be introduced into the thread-like endless carrier.

In a preferred embodiment of the invention, the structured elements are rounded at their free ends to prevent injury to the teeth and the gum, as may be caused by the conventional covering having fibers comprising cut fine bristles, since the ends thereof have relatively sharp edges. Moreover, the round ends of the structured elements facilitate the folding-over thereof when guided through narrow spaces.

In a first embodiment, the cleaning element may comprise a plurality of similar structured elements and support bodies on the endless carrier. Alternatively, structured elements and support bodies made from different materials and with differing shapes can be disposed on the endless carrier. Some support bodies may e.g. be provided with structured elements having care products, medicine or abrasive materials, with their neighboring support bodies having structured elements without such additional substances. The differences could be indicated to the user using corresponding colors.

In order to use the cleaning element as dental floss for cleaning teeth, the user must cut a section off the endless carrier and hold the ends thereof with his/her hands. This is facilitated by disposing holding means on the endless carrier at defined distances, which consist of plastic and are preferentially injection molded thereon. The user simply cuts the endless carrier behind the holding means and can then grasp the cut-off section at the holding means to facilitate cleaning of the teeth. The holding elements may be injection molded enlargements or plates to facilitate grasping of the separated section of the endless carrier.

In addition, the endless carrier may have orientation elements at defined distances, which are preferentially injection molded thereon, and which indicate where the endless carrier should be cut, both during production of the cleaning element as well as during its use.

In certain applications, it may be reasonable or desirable to connect the section separated from the endless carrier to form a continuous loop. This may be achieved by injection molding connecting elements onto the endless carrier which may be connected to each other after separating off a section, to form a continuous loop.

A dental floss is usually accommodated in a casing from which a user can pull out the desired length. The casing has a cutting device with which the user can cut off the pulled out section of the dental floss. If the cutting device is a moveable knife, the dental floss may comprise triggering means at defined distances which trigger the knife as soon as they pass a corresponding stop.

Previous applications for the cleaning element were restricted to its use as dental floss. However, in a further advantageous application, the endless carrier is subdivided into short sections and these short sections are then used in a conventional manner as bristles in a brush, in particular a tooth brush. Towards this end, the structured elements and/or the support bodies may be made from a hard or elastomeric plastic.

The above-mentioned object is achieved with respect to a method in that the structured elements are formed by injection molding a plastic, in particular an elastomeric plastic, onto a thread-like endless carrier. A support body, enclosing the endless carrier, is preferentially simultaneously injection molded and is axially secured on the carrier by the injection pressure and the resulting deformation of the endless carrier in a radially inward direction. If a two or multiple component method is used, structured elements and/or support bodies of different materials may also be applied to an endless carrier. Further features of the method may be extracted from the above description of the cleaning element.

Further details and features of the invention can be extracted from the following description of embodiments with reference to the enclosed drawing.

BRIEF DESCRIPTION OF THE INVENTION

FIG. 1 shows a side view of sections of a cleaning element according to a first embodiment;

FIG. 2 shows a modification of the cleaning element according to FIG. 1;

FIG. 3 shows a side view of a cleaning element in a further embodiment;

FIG. 4 shows an alternative embodiment of the cleaning element; and

FIG. 5 shows a cleaning element with injection molded holding means.

DESCRIPTION OF THE PREFERRED EMBODIMENT

As seen in FIG. 1, a cleaning element 10 according to the invention, which is preferentially used for cleaning teeth, comprises a flexible thread-like endless carrier 11, which may be a monofile or a multifile.

An enclosing, tube-shaped support body 12 is injection molded onto sections of the endless carrier 11 which are spaced apart from one another. The support body 12 comprises a plurality of structured elements 13 on its outer surface in the form of cone-shaped projections protruding in different directions radially outwardly, which are rounded on their outer free ends. The support body 12 and the structured elements 13 are made from an elastomeric plastic and formed as a single piece.

In the variant of the embodiment shown in FIG. 1, the sections of the thread-like endless carrier 11 disposed between the neighboring support bodies 12 are not covered. In the modified embodiment of FIG. 2, these intermediate sections are enclosed with the elastomeric plastic forming the support bodies 12 and the structured elements 13, wherein the outer diameter at these sections is smaller than that of the support body 12.

FIG. 3 shows a cleaning element whose support body 12 comprises transverse circumferential ribs 13 projecting from its outer side to form the structured elements. Moreover, the diameter of the support body increases slightly from its ends towards its center to thereby improve the cleaning action.

FIG. 4 shows an embodiment having different support bodies 12 with various structured elements 13 disposed on the thread-like endless carrier 11.

When the cleaning element is used as dental floss in the conventional sense, the user must cut off a section from the thread-like endless carrier, hold it and pull it through the interdental spaces. To facilitate holding of the section, the cleaning element shown in FIG. 5 comprises two ball-shaped holding means injection molded onto the endless carrier 11 at defined, small mutual separation. The user separates the thread-like endless carrier 11 between the two holding means 14, as indicated by arrow T, to thereby obtain one section of the cleaning element comprising a holding means 14 at each end.

I claim:

1. A method of manufacturing a cleaning element and a tooth cleaning element, the method comprising the steps of:

preparing a flexible thread-like endless carrier; and injecting plastic onto said endless carrier to form at least one tube-shaped support body and to form structured plastic elements radially projecting from an outer surface of said tube-shaped support body, wherein said tube-shaped support body bears said structured plastic elements, said structured plastic elements and said endless carrier being structured and dimensioned for application of said structured plastic elements to a surface for cleaning that surface.

2. The method of claim 1, wherein said plastic is injected onto sections of said endless carrier.

3. The method of claim 1, wherein said plastic is an elastomeric plastic.

4. The method of claim 1, wherein a plurality of support bodies are injected onto said endless carrier, said plurality of support bodies being spaced apart from one another.

5. The method of claim 4, wherein at least one of said support bodies and said structured elements have cavities.

6. The method of claim 5, wherein said cavities accommodate at least one of a medical care product, a lubricating agent, and an abrasive agent.

7. The method of claim 6, further comprising the step of filling said cavities using a hollow needle.

8. The method of claim 4, wherein said support bodies enclose said endless carrier.

9. The method of claim 4, comprising encasing portions of said endless carrier, located between adjacent support bodies, with said plastic.

10. The method of claim 4, wherein said outer surfaces of said support bodies are at least one of corrugated and fluted.

11. The method of claim 4, wherein said support bodies have at least one of a round, an oval and a polygonal cross-sectional shape.

12. The method of claim 4, further comprising disposing at least one of a medical care product, a lubricating agent, and an abrasive agent on an outside of at least one of said support bodies and said structured elements.

13. The method of claim 4, wherein said support bodies have differing surface configurations.

14. The method of claim 4, wherein said support bodies are made from differing plastics.

15. The method of claim 1, wherein said endless carrier consists essentially of one of a thread, a twisted thread, a wire, a multifile, a monofile, a tape, and a wick.

16. The method of claim 1, wherein said structured elements consist essentially of at least one of radially projecting nubs, bristles, and ribs.

17. The method of claim 1, wherein said structured elements are rounded at their free ends.

18. The method of claim 1, further comprising disposing holding means on said endless carrier at defined separations.

19. The method of claim 1, further comprising disposing connecting elements on said endless carrier at defined distances.

20. The method of claim 1, further comprising disposing triggering means for a cutting device on said endless carrier at defined distances.

21. The method of claim 1, further comprising the step of using a short section of the cleaning element as a bristle in at least one of a brush and a tooth brush.

22. The method of claim 1, wherein said support body is made from a same plastic as said structured elements.

* * * * *

UNITED STATES PATENT AND TRADEMARK OFFICE
CERTIFICATE OF CORRECTION

PATENT NO. : 6,672,316 B1
DATED : January 6, 2004
INVENTOR(S) : Weihrauch, Georg It is certified that error appears in the above-identified patent and that said Letters Patent is hereby corrected as shown below:

Drawings,
Please replace sheet one of the figures containing figures 1 and 2 with the enclosed sheet.

Column 6,
Line 5, should read:
-- The method of claim 4, comprising encasing portions of said endless carrier, located between adjacent support bodies, with said plastic. --.

Signed and Sealed this

Twenty-fourth Day of August, 2004

JON W. DUDAS
*Director of the United States Patent and Trademark Office*

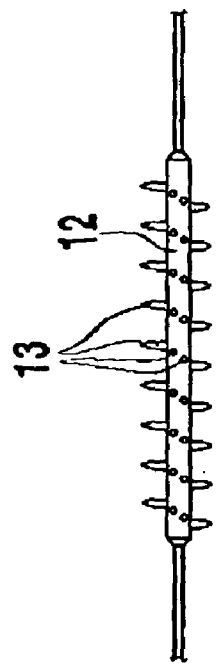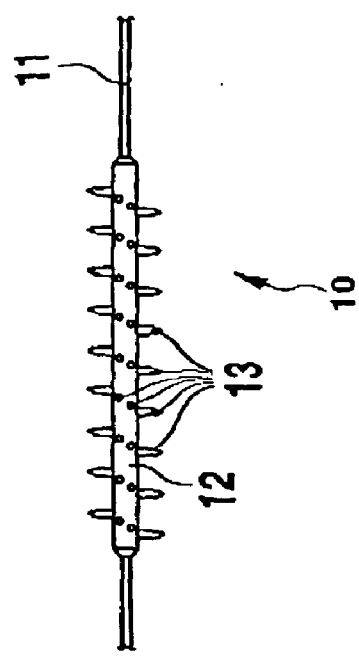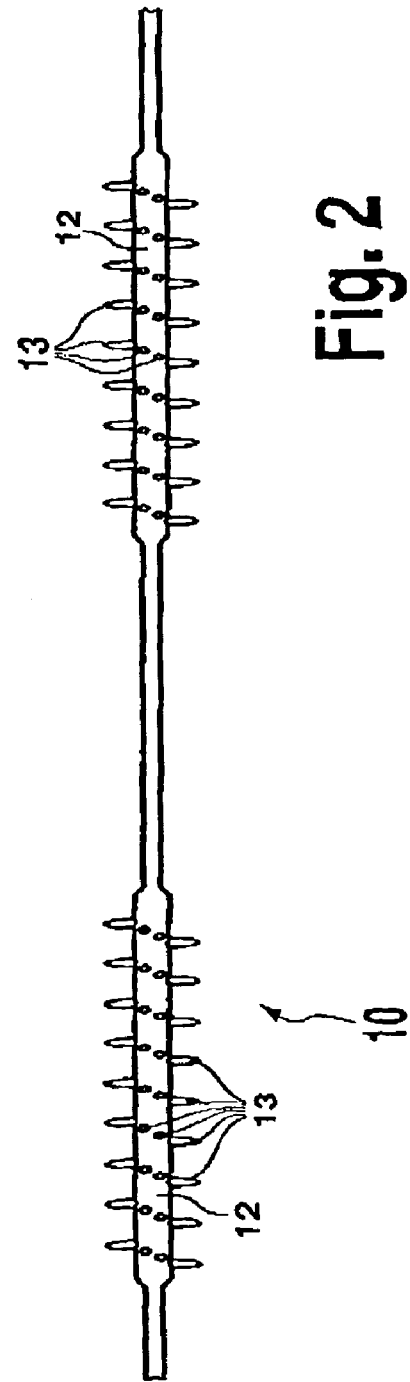

UNITED STATES PATENT AND TRADEMARK OFFICE
CERTIFICATE OF CORRECTION

PATENT NO. : 6,672,316 B1
DATED : January 6, 2004
INVENTOR(S) : Weihrauch, Georg It is certified that error appears in the above-identified patent and that said Letters Patent is hereby corrected as shown below:

Drawings,
Please replace sheet one of the figures containing figures 1 and 2 with the enclosed sheet.

Column 1,
Line 5, delete "Translation of PCT/EP00/01295 as filed on Feb. 17, 2000".

Column 6,
Line 5, should read:
-- The method of claim 4, further comprising encasing portions of said endless carrier, located between adjacent support bodies, with said plastic. --.

This certificate supersedes Certificate of Correction issued August 24, 2004.

Signed and Sealed this

Fifth Day of July, 2005

JON W. DUDAS
*Director of the United States Patent and Trademark Office*

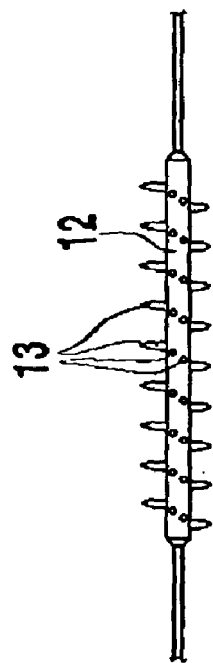
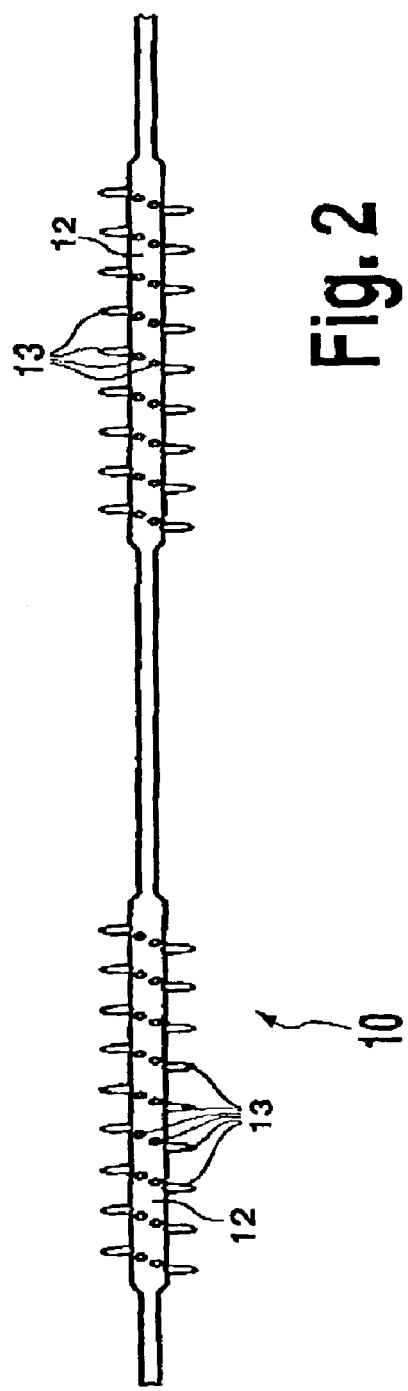
Fig. 1
Fig. 2